United States Patent [19]

Shiokawa et al.

[11] Patent Number: 5,204,359
[45] Date of Patent: Apr. 20, 1993

[54] INSECTICIDALLY ACTIVE NITRO COMPOUNDS

[75] Inventors: Kozo Shiokawa, Kanagawa; Shinichi Tsuboi, Tokyo; Koichi Moriya, Tokyo; Yumi Hattori, Tokyo; Ikuro Honda, Tokyo; Katsuhiko Shibuya, Tokyo, all of Japan

[73] Assignee: Nihon Bayer Agrochem K.K., Tokyo, Japan

[21] Appl. No.: 757,864

[22] Filed: Sep. 11, 1991

Related U.S. Application Data

[62] Division of Ser. No. 478,862, Feb. 12, 1990, Pat. No. 5,084,467.

[30] Foreign Application Priority Data

Feb. 13, 1989 [JP] Japan ................... 1-31145

[51] Int. Cl.$^5$ ............... A01M 1/20; A01N 43/40; A01N 43/60; A01N 43/54
[52] U.S. Cl. .................. 514/332; 544/111; 544/124; 544/127; 544/333; 544/334; 544/335; 544/336; 544/360; 544/369; 544/371; 544/409; 546/211; 546/209; 546/256; 546/262; 546/265; 546/278; 546/332; 546/264; 546/330; 546/277; 548/127; 548/198; 548/199; 548/235; 548/236; 548/247; 548/248; 548/566; 548/365.1; 548/364.1; 548/375.1
[58] Field of Search ............... 546/338, 264, 256, 279, 546/277, 275, 283, 262, 330, 336, 265, 209, 211, 278, 332; 544/296, 242, 357, 360, 333, 334, 335, 336, 409, 111, 124, 127, 369, 371, 295; 548/128, 198, 236, 235, 247, 127, 199, 248, 378, 566; 514/332

[56] References Cited

U.S. PATENT DOCUMENTS 4,499,097 2/1985 Tomcufcik et al. ............. 514/341
4,567,188 1/1986 Niemers et al. ................ 546/284
4,918,086 4/1990 Gsell ........................... 514/351

FOREIGN PATENT DOCUMENTS 0104423 4/1984 European Pat. Off. ......... 546/284
0302389 2/1989 European Pat. Off. ......... 546/284
303570 2/1989 European Pat. Off. ......... 546/284
03022389 2/1989 European Pat. Off. ......... 546/284
302833 8/1989 European Pat. Off. ......... 546/284
234064 10/1987 Japan .......................... 546/284
233903 9/1988 Japan .......................... 546/284
2201596 9/1988 United Kingdom ............. 546/284

OTHER PUBLICATIONS

Nihon Kagaku Zasshi, vol. 83, pp. 218–222, 1962.

Primary Examiner—C. Warren Ivy
Assistant Examiner—D. Margaret Mach

[57] ABSTRACT

Insecticidally active nitro compounds of the formula $$Z-CH(R^1)-N(R^2)-C(R^3)=Y-NO_2 \quad (I)$$

wherein
R$^1$ is hydrogen, cyano or alkyl,
R$^2$ is hydrogen or an organic radical,
R$^3$ is $$-O-R^4, -S-R^4 \text{ or } -N(R^5)-R^6,$$

R$^4$ is an organic radical,
R$^5$ and R$^6$ are hydrogen or organic radicals,
Y is CH or N, and
Z is an optionally substituted 5- or 6-membered heterocyclic group, with certain conditions and exceptions.

9 Claims, No Drawings

INSECTICIDALLY ACTIVE NITRO COMPOUNDS

This is a division of application Ser. No. 478,862, filed Feb. 12, 1990, now U.S. Pat. No. 5,084,467.

The present invention relates to novel nitro compounds, to processes for their preparation and to their use as insecticides.

It has already been disclosed that a certain group of 2-nitro-1,1-ethenediamines is useful as medicaments which influence the circulation, in particular as hypotensive agents (see the U.S. Pat. No. 4,567,188), a certain group of N-cyanoisothioureas is useful as medicaments for treating ulcers (see Japanese Patent Laid-open No. 234,064/1987), the N-cyanoisothioureas disclosed in the above Japanese patent application have also a function for controlling insects and plant-destructive nematodes (see Japanese Patent Laid-open No. 233,903 and EP-A 303,570), and that a certain group of α-unsaturated amines has insecticidal/miticidal activity (see EP-A 0302389).

There have now been found novel nitro compounds of the formula (I)

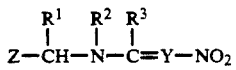

(I)

wherein $R^1$ is hydrogen, cyano or $C_{1-4}$ alkyl, $R^2$ is hydrogen, $C_{1-6}$ alkyl, $C_{3-4}$ alkenyl, $C_{3-4}$ alkynyl, $C_{3-8}$ cycloalkyl optionally substituted by $C_{1-2}$ alkyl, optionally substituted phenyl, optionally substituted benzyl, $C_{1-4}$ alkoxy or —$(CH_2)_n$—Z, in which n is 1 or 2 and Z has the same meaning as stated hereinafter, $R^3$ is

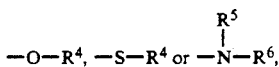

in which $R^4$ is $C_{1-6}$ alkyl, $C_{3-4}$ alkenyl, $C_{3-4}$ alkynyl, $C_{3-8}$ cycloalkyl, optionally substituted benzyl or —$(CH_2)_n$—Z, in which n has the same meanings as stated above and Z has the same meanings as stated hereinafter, $R^5$ and $R^6$ are the same or different and stand for hydrogen, $C_{1-9}$ alkyl optionally substituted by at least one substituent selected from the group consisting of mercapto, $C_{1-2}$ alkoxy, $C_{3-6}$ cycloalkyl, amino, $C_{1-2}$ mono-alkylamino, $C_{2-4}$ (in total) dialkylamino, $C_{1-2}$ alkoxy-carbonyl and cyano; or $R^5$ and $R^6$ are the same or different and stand for $C_{3-4}$ alkenyl optionally substituted by halogen, $C_{3-4}$ alkynyl, optionally substituted phenyl, optionally substituted benzyl, $C_{1-4}$ alkoxy, hydroxy, formyl, $C_{1-4}$ alkylamino, $C_{2-4}$ (in total) dialkylamino, amino, acyl, 5- or 6-membered heterocyclic group optionally substituted by halogen or $C_{1-4}$ alkyl, or —$CH_2$—Z in which Z has the same meanings as stated hereinafter, or $R^5$ and $R^6$ may form, together with the adjacent nitrogen atom, a 3 to 7 membered cyclic group which may be substituted by $C_{1-2}$ alkyl and may have an N, O or S atom as a ring member, besides the adjacent nitrogen atom, Y is CH or N, and Z is an optionally substituted 5- or 6-membered heterocyclic group which has at least one hetero atom selected from N, O and S and which may be benzo-fused, provided that where Y is CH, then $R^1$ is cyano or $C_{1-4}$ alkyl, and with the exception of the case where $R^1$ and $R^2$ are hydrogen or $C_{1-4}$ alkyl, $R^3$ is —S—$R^4$ or

in which $R^4$ is $C_{1-4}$ alkyl, $R^5$ and $R^6$ are hydrogen or $C_{1-4}$ alkyl, Y is CH or N, and Z is 5- or 6-membered heterocyclic group having at least one nitrogen atom which may be substituted by halogen or $C_{1-4}$ alkyl.

The compounds of the formula (I) can be obtained by a process in which a): (in the case where $R^3$ is —S—$R^4$ and y is CH, then $R^1$ is replaced by $R^7$, in which $R^7$ is cyano or $C_{1-4}$ alkyl) compounds of the formula (II)

(II)

wherein $R^4$ has the same meanings as mentioned above, are reacted with compounds of the formula (III)

(III)

wherein $R^7$, $R^2$ and z have the same meanings as stated above, in the presence of inert solvents, or b): (in the case where $R^3$ is

and Y is CH, then $R^1$ is replaced by $R^7$)

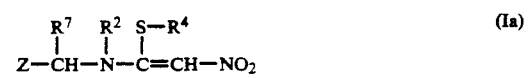

(Ia)

wherein $R^7$, $R^2$, $R^4$ and Z have the same meanings as mentioned above, are reacted with compounds of the formula (IV)

(IV)

wherein $R^5$ and $R^6$ have the same meanings as mentioned above, in the presence of inert solvents, or c): (in the case where $R^3$ is

and Y is CH) compounds of the formula (V)

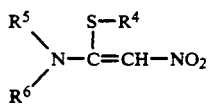 (V)

wherein $R^4$, $R^5$ and $R^6$ have the same meanings as mentioned above, are reacted with the aforementioned compounds of the formula (III) in the presence of inert solvents, or d): (in the case where $R^3$ is $-S-R^4$ and Y is N) compounds of the formula (VI)

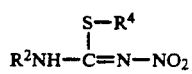 (VI)

wherein $R^2$ and $R^4$ have the same meanings as mentioned above, are reacted with compounds of the formula (VII)

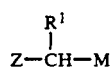 (VII)

wherein $R^1$ and Z have the same meanings as mentioned above, and M is halogen, methanesulfonyloxy or tosyloxy, in the presence of inert solvents, and if appropriate in the presence of acid binders, or e): (in the case where $R^3$ is

and Y is N) compounds of the formula (Id)

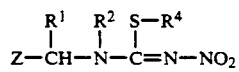 (Id)

wherein $R^1$, $R^2$, $R^4$ and Z have the same meanings as mentioned above, are reacted with the aforementioned compounds of the formula (IV) in the presence of inert solvents, or f): (in the case where $R^3$ is $-O-R^4$ and Y is N) compounds of the formula (VIII)

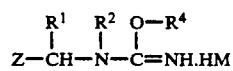 (VIII)

wherein $R^1$, $R^2$, $R^4$, Z and M have the same meanings as mentioned above, are reacted with fuming nitric acid in the presence of concentrated sulfuric acid, and if appropriate in the presence of inert solvents, or g): (in the case where $R^3$ is $-O-R^4$ and Y is CH, then $R^1$ is replaced by $R^7$) compounds of the formula (IX)

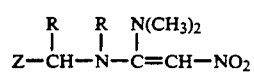 (IX)

wherein $R^7$, $R^2$ and Z have the same meanings as mentioned above, are reacted with compounds of the formula (X)

$R^4-OH$ (X)

wherein $R^4$ has the same meaning as mentioned above, in the presence of inert solvents.

The novel nitro compounds exhibit powerful insecticidal properties.

Surprisingly, the nitro compounds according to the invention exhibit a substantially greater insecticidal action than those known from the above cited prior art.

In the formulae, alkyl or the alkyl parts of the mentioned radicals are straight-chain or branched, and where the alkyl contains 1 to 9 carbons, then it contains preferably 1 to 6, particularly preferably to 4, and where the alkyl contains 1 to 6 carbons, then it contains preferably 1 to 4, particularly preferably 1 to 3, and where the alkyl contains 1 to 4, then it contains preferably 1 to 3, particularly preferably 1 to 2, carbon atoms. As examples there may be mentioned: methyl, ethyl, n- and i-propyl-, n-, i-, s- and t-butyl, n-pentyl, n-hexyl, n-octyl and n-nonyl.

In the formulae, $C_{3-4}$ alkenyl is 1-propenyl, allyl and 1-, 2- and 3-butenyl. Preferred and also particularly preferred is allyl.

In the formulae, $C_{3-4}$ alkynyl is 1-propynyl, propargyl, 1-butyl-1-yl and 2-butyl-1-yl. Preferred and also particularly preferred is propargyl.

In the formulae, $C_{3-8}$ cycloalkyl contains preferably 3 to 6, particularly preferably cyclohexyl, and $C_{3-6}$ cycloalkyl is preferably cyclohexyl, and also particularly preferably cyclohexyl.

In the formulae, halogen denotes fluorine, chlorine, bromine and iodine, preferably fluorine, chlorine and bromine, particularly fluorine and chlorine.

In the formulae, phenyl and benzyl described as being optionally substituted may contain one or more identical or different substituents. As preferred substituents there may be mentioned halogen such as fluorine, chlorine and bromine, preferably chlorine.

In the formulae, 3 to 7 membered cyclic group is preferably 3 to 6 membered cyclic group, particularly preferably pyrrolidino, piperidino 2-methylpiperidino, morpholino, piperazino or 1-isoxazolyl.

In the formulae, $C_{2-4}$ (in total) dialkylamino is preferably and also particularly preferably dimethylamino.

In the formulae, 5- or 6-membered heterocyclic group described as being optionally substituted may contain one or more identical or different substituents such as halogen or $C_{1-4}$ alkyl optionally substituted by halogen. As examples there may be mentioned: fluorine, chlorine, bromine, idoine, trifluoromethyl, methyl, ethyl, n- and i-propyl, and n-, i-, s- and t-butyl. Preferred and also particularly preferred are chlorine or methyl. The substituent may be in all possible positions of the 5- or 6-membered heterocyclic group. Preferably it is in the 6 position of the 3-pyridyl ring and in the 2 position of the 5-thiazolyl ring.

In the formulae, 5- or 6-membered heterocyclic group contains preferably one or two nitrogen atoms, or one nitrogen atom and either one oxygen atom or one sulfur atom, and said heterocyclic group may be benzo-fused. As preferred examples there may be mentioned: 3-pyridyl, 5-thiazolyl, 5-isoxazolyl, 1,2,5-thiadiazol-3-yl, 4-pyrazolyl, 5-oxazolyl, 5-pyrimidinyl, and 2-pyrazinyl.

Among the nitro compounds according to the invention, of the formula (I), preferred compounds are those in which $R^1$ is hydrogen, methyl, ethyl or n-propyl, $R^2$ is hydrogen, $C_{1-4}$ alkyl, allyl, propargyl, $C_{5-6}$ cycloalkyl optionally substituted by methyl, phenyl optionally substituted by halogen, benzyl optionally substituted by halogen, $C_{1-3}$ alkoxy or —CH$_2$—$Z^1$ in which $Z^1$ is pyridyl optionally substituted by halogen, $R^3$ is —O—$R^4$, —S—$R^4$ or

in which $R^4$ is $C_{1-4}$ alkyl, allyl, $C_{3-6}$ cycloalkyl, phenyl optionally substituted by halogen, benzyl optionally substituted by halogen or —CH$_2$—$Z^1$ in which $Z^1$ has the same meaning as stated above, $R^5$ and $R^6$ are hydrogen, $C_{1-6}$ alkyl optionally substituted by at least one substituent selected from the group consisting of mercapto, methoxy, cyclohexyl, amino, methylamino, dimethylamino, methoxycarbonyl and cyano, allyl optionally substituted by chlorine, propargyl, phenyl optionally substituted by chlorine, benzyl optionally substituted by chlorine, $C_{1-3}$ alkoxy, hydroxy, formyl, $C_{1-3}$ alkylamino, dimethylamino, amino, acetyl, benzoyl, 6-chloronicotinoyl, pyridyl optionally substituted by chlorine or methyl, or —CH$_2$—$Z^2$ in which $Z^2$ represents the definition of $Z^1$ hereinbefore and 5-thiazolyl optionally substituted by chlorine, in addition $R^5$ and $R^6$ may form, together with the adjacent nitrogen atom, 3 to 6 membered cyclic group which may be substituted by methyl and may have an N, O or S atom as a ring member, besides the adjacent nitrogen atom, Y is CH or N, and Z is a 5-membered heterocyclic group which has one or two nitrogen atoms, or one nitrogen atom and either one oxygen atom or one sulfur atom and may be substituted by halogen or $C_{1-4}$ alkyl, or a 6-membered heterocyclic group which has one or two nitrogen atoms and may be substituted by halogen or $C_{1-4}$ alkyl optionally substituted by halogen and said 5- or 6-membered heterocyclic groups may be benzo-fused, provided that where Y is CH, then $R^1$ is methyl, ethyl or n-propyl, and with the exception of the case where $R^1$ is hydrogen, methyl, ethyl or n-propyl, $R^2$ is hydrogen or $C_{1-4}$ alkyl, $R^3$ is —S—$R^4$ or

in which $R^4$ is $C_{1-4}$ alkyl, $R^5$ and $R^6$ are hydrogen or $C_{1-4}$ alkyl, Y is CH or N, and Z is 5- or 6-membered heterocyclic group having at least one nitrogen atom which may be substituted by halogen or $C_{1-4}$ alkyl optionally substituted by halogen.

More preferred nitro compounds of the formula (I) are those in which $R^1$ is hydrogen, methyl or ethyl, $R^2$ is hydrogen, methyl, ethyl, n-propyl, allyl, propargyl, cyclohexyl, phenyl optionally substituted by chlorine, benzyl optionally substituted by chlorine, $C_{1-2}$ alkoxy or 2-chloro-5-pyridylmethyl, $R^3$ is

in which $R^5$ and $R^6$ are hydrogen, $C_{1-4}$ alkyl optionally substituted by at least one substituent selected from the group consisting of mercapto, methoxy, cyclohexyl, amino, methylamino, dimethylamino, methoxycarbonyl and cyano, allyl optionally substituted by chlorine, benzyl optionally substituted by chlorine, $C_{1-2}$ alkoxy, hydroxy, formyl, $C_{1-2}$ alkylamino, dimethylamino, amino, acetyl, benzoyl, 6-chloronicotinoyl, 2-chloro-5-pyridyl, 2-chloro-5-pyridylmethyl or 2-chloro-5-thiazolylmethyl, in addition $R^5$ and $R^6$ may represent, together with the adjacent nitrogen atom, pyrrolidino, piperidino, 2-methylpiperidino, morpholino, piperazino or 1-isoxazolyl, Y is CH or N, and Z is a 5-membered heterocyclic group which has one or two nitrogen atoms, or one nitrogen atom and either one oxygen atom or one sulfur atom and may be substituted by halogen or $C_{1-2}$ alkyl optionally substituted by fluorine, or a 6-membered heterocyclic group which has one or two nitrogen atoms and may be substituted by halogen or $C_{1-2}$ alkyl optionally substituted by fluorine, provided that when Y is CH, then $R^1$ is methyl or ethyl, and with the exception of the case where $R^1$ is hydrogen, methyl or ethyl, $R^2$ is hydrogen, methyl, ethyl or n-propyl, $R^3$ is

in which $R^5$ and $R^6$ are hydrogen or $C_{1-4}$ alkyl, Y is CH or N, and Z is a 5- or 6-membered heterocyclic group having at least one nitrogen atom which may be substituted by halogen or $C_{1-2}$ alkyl optionally substituted by fluorine.

Much more preferred nitro compounds of the formula (I) are those in which $R^1$ is hydrogen, methyl or ethyl, $R^2$ is hydrogen, methyl, ethyl, n-propyl, allyl, propargyl, cyclohexyl, phenyl optionally substituted by chlorine, benzyl optionally substituted by chlorine, $C_{1-2}$ alkoxy or 2-chloro-5-pyridylmethyl, $R^3$ is

in which $R^5$ and $R^6$ are hydrogen, $C_{1-4}$ alkyl optionally substituted by at least one substituent selected from the group consisting of mercapto, methoxy, cyclohexyl, amino, methylamino, dimethylamino, methoxycarbonyl and cyano, allyl optionally substituted by chlorine, benzyl optionally substituted by chlorine, $C_{1-2}$ alkoxy, hydroxy, formyl, $C_{1-2}$ alkylamino, dimethylamino, amino, acetyl, benzoyl, 6-chloronicotinoyl, 2-chloro-5-pyridyl, 2-chloro-5-pyridylmethyl or 2-chloro-5-thiazolylmethyl, in addition $R^5$ and $R^6$ may represent, together with the adjacent nitrogen atom, pyrrolidino, piperidino, 2-methylpiperidino, morpholino, piperazino or 1-isoxazolyl, Y is CH or N, and Z is a 5-membered heterocyclic group which has one or two nitrogen atoms, or one nitrogen atom and either one oxygen atom or one sulfur atom and may be substituted by halogen or $C_{1-2}$ alkyl optionally substituted by fluorine, or 6-membered heterocyclic group which has one or two nitrogen atoms and may be substituted by halogen or $C_{1-2}$ alkyl optionally substituted by fluorine, provided that where Y is CH, then $R^1$ is methyl or ethyl, and that where $R^2$ is hydrogen and $R^3$ is

in which either $R^5$ or $R^6$ is hydrogen, the other is allyl, phenyl optionally substituted by chlorine, 2-chloro-5-pyridylmethyl or 2-chloro-5-thiazolylmethyl, then Y is N, and with the exception of the case were $R^1$ is hydrogen, methyl or ethyl, $R^2$ is hydrogen, methyl, ethyl or n-propyl,
$R^3$ is

in which $R^5$ and $R^6$ are hydrogen or $C_{1-4}$ alkyl, Y is CH or N, and Z is a 5- or 6-membered heterocyclic group having at least one nitrogen atom which may be substituted by halogen or $C_{1-2}$ alkyl optionally substituted by fluorine.

Very particularly preferred nitro compounds of the formula (I) are those in which
$R^1$ is hydrogen or methyl
$R^2$ is hydrogen, methyl, ethyl, allyl, propargyl, methoxy or 2-chloro-5-pyridylmethyl,
$R^3$ is

in which $R^5$ and $R^6$ are hydrogen, $C_{1-2}$ alkyl optionally substituted by at least one substituent selected from the group consisting of mercapto, methoxy, cyclohexyl, amino, methylamino, dimethylamino, methoxycarbonyl and cyano, allyl, 2-chloroallyl, benzyl, 3- or 4-chlorobenzyl, methoxy, hydroxy, formyl, methyamino, dimethylamino, amino, acetyl, benzoyl, 6-chloronicotinoyl, 2-chloro-5-pyridyl or 2-chloro-5-pyridylmethyl,
Y is N, and
Z is 2-chloro-5-pyridyl, with the exception of the case where $R^1$ is hydrogen or methyl,
$R^2$ is hydrogen, methyl or ethyl,
$R^3$ is

in which $R^5$ and $R^6$ are hydrogen or $C_{1-2}$ alkyl, Y is N, and Z is 2-chloro-5-pyridyl.

Specifically, the following compounds may be mentioned:
1-{N-[1-(2-chloro-5-pyridyl)ethyl]-N-methyamino}-1-(2-chloro-5-pyridylmethyl)amino-2-nitroethylene,
1-allyl-3-(2-chloro-5-pyridylmethyl)-2-nitroguanidine, and
1,3-bis-(2-chloro-5-pyridylmethyl)-2-nitroguanidine.

If, for example, in the above process a), 1,1-bis-methylthio-2-nitroethylene and 1-(2-trifluoromethyl-5-thiazolyl)ethylamine are used as starting materials, the course of the reaction can be represented by the following equation:

$(CH_3S)_2C=CH-NO_2 +$

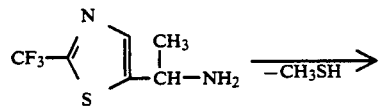

If, for example, in the above process b), 1-[1-(2-chloro-5-pyridyl)ethylamino]-1-methylthio-2-nitroethylene and 2-chloro-5-pyridylmethylamine are used as starting materials, the course of the reaction can be represented by the following equation:

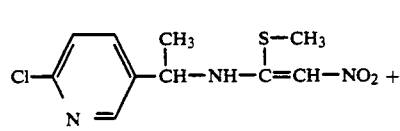

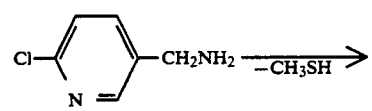

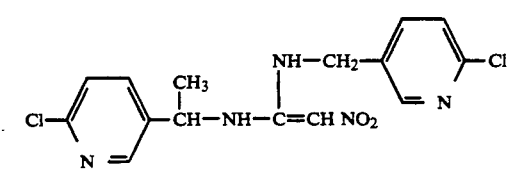

If, for example, in the above process c), 1-allylamino-1-methylthio-2-nitroethylene and N-methyl-1-(2-chloro-5-pyridyl)ethylamine are used as starting materials, the course of the reaction can be represented by the following equation:

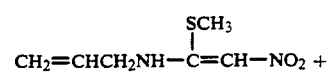

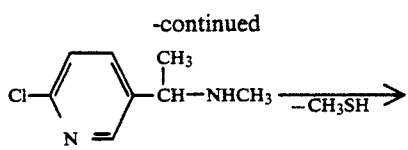

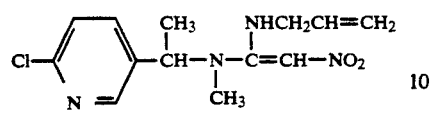

If, for example, in the above process d), 3-nitro-2-methylisothiourea and 5-chloromethyl-2-trifluoromethylpyridine are used as starting materials, the course of the reaction can be represented by the following equation:

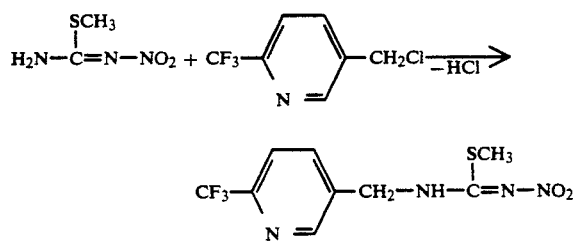

If, for example, in the above process e), 1-(2-chloro-5-pyridylmethyl)-3-nitro-2-methylisothiourea and propargylamine are used as starting materials, the course of the reaction can be represented by the following equation:

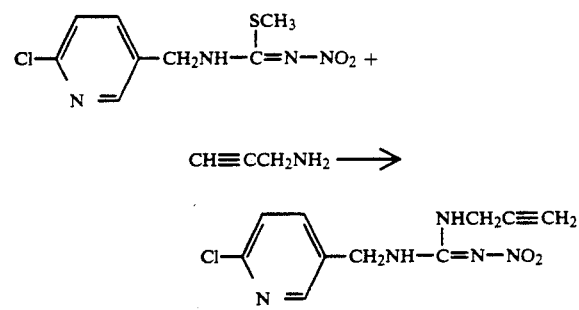

If, for example, in the above process f), 1-(2-chloro-5-pyridylmethyl)-2-methylisourea is used as a starting material, the course of the reaction can be represented by the following equation:

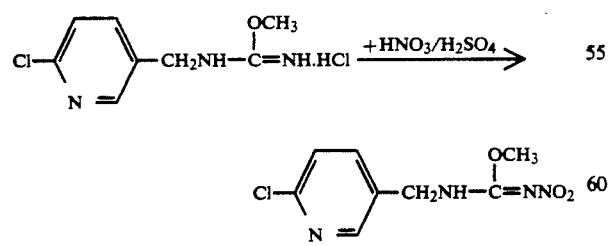

If, for example, in the above process g), 1-[1-(2-chloro-5-pyridyl)ethylamino]-1-dimethylamino-2-nitroethylene and ethanol are used as starting materials, the course of the reaction can be represented by the following equation:

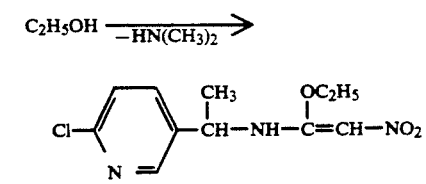

In the process a), the compounds of the formula (II) as a starting material mean ones based on the aforementioned definition of $R^4$.

In the formula (II), $R^4$ preferably has the meaning already given above.

The compounds of the formula (II) include known compounds (see e.g. Chem. Ber., vol. 100, pages 591–604, 1967) and, as an example, 1,1-bis-methylthio-2-nitroethylene can be exemplified.

The compounds of the formula (III) as a starting material means compounds based on the aforementioned definitions of $R^7$, $R^2$ and Z.

In the formula (III), $R^7$, $R^2$ and Z preferably have the meanings already given above.

The compounds of the formula (III) include in part known compounds [see Nihon Kagaku Zasshi (Periodical of Japanese Chemistry) vol. 83, pages 218–222, 1962, J. Chem. Soc. Perkin I, 1979, pages 2364–2368].

The compounds of the formula (III), for instance, may be prepared in accordance with a method described in the above reference, J. Chem. Soc. Perkin I, 1979, pages 2364–2368.

The compounds of the formula (III), in case where $R^2$ is hydrogen, can be obtained when compounds of the formula (XI)

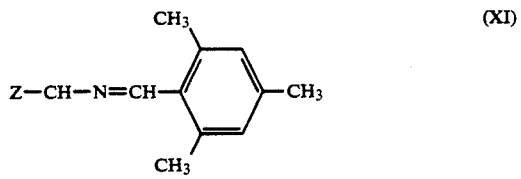

wherein $R^7$ and Z have the same meanings as mentioned above, are hydrolyzed.

The compounds of the formula (XI) can be obtained when Schiff-bases of the formula (XII)

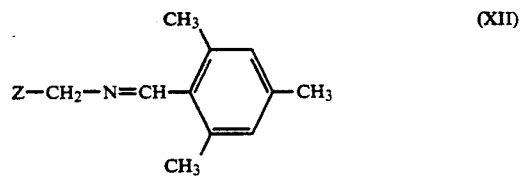

wherein Z has the same meaning as mentioned above, are alkylated by reacting with compounds of the formula (XIII)

$R^7$—Hal                        (XIII)

wherein R[7] has the same meaning as mentioned above, and Hal is halogen,
in the presence of catalytic amounts of butyl-lithium and in the presence of an inert solvent such as tetrahydrofuran.

The compounds of the formula (XII) can be obtained when compounds of the formula (XIV)

$$Z-CH_2-NH_2 \quad \text{(XIV)}$$

wherein Z has the same meaning as mentioned above, are reacted with mesitaldehyde in the presence of inert solvents.

The compounds of the formula (XIV) include known ones described in the U.S. Pat. No. 4,499,097, and the aforesaid Nihon Kagaku Zasshi.

In the process b), the compounds of the formula (Ia) as a starting material correspond to a part of the compounds of the formula (I) which can be prepared by the above process a).

The compounds of the formula (IV) as a starting material mean ones based on the aforementioned definitions of R[5] and R[6].

In the formula (IV), R[5] and R[6] preferably have the meanings already given above.

The compounds of the formula (IV) are well known in the field of organic chemistry and, as examples, there may be mentioned: methylamine, diethylamine and the like.

In the process c), the compounds of the formula (V) as a starting material mean ones based on the aforementioned definitions of R[4], R[5] and R[6].

In the formula (V), R[4], R[5] and R[6] preferably have the meanings already given above.

The compounds of the formula (V) can in general be obtained when the aforementioned compounds of the formula (II) are reacted with the aforementioned compounds of the formula (IV).

As examples of the compounds of the formula (V), there may be mentioned: 1-allylamino-1-methylthio-2-nitroethylene, 1-(2-chloro-5-pyridylmethylamino)-1-methylthio-2-nitroethylene, and the like.

In the process d), the compounds of the formula (VI) as a starting material mean ones based on the aforementioned definitions of R[2] and R[4].

In the formula (VI), R[2] and R[4] preferably have the meanings already given above.

The compounds of the formula (VI) are known (see e.g. J. Am. Chem. Soc., vol. 76, pages 1877–1879, 1954) and, as examples, there may be mentioned: 3-nitro-2-methylisothiourea, 1,2-dimethyl-3-nitroisothiourea, 1,1,2-trimethyl-3-nitroisothiourea, and the like.

The compounds of the formula (VII) as a starting material mean those based on the aforementioned definitions of R[1], Z and M.

In the formula (VII), R[1] and Z preferably have the meanings already given above, and M preferably represents chlorine, bromine or tosyloxy.

The compounds of the formula (VII) include known compounds (see Japanese Patent Laid-open Nos. 178,981/1986, 178,982/1986 or 183,271/1986) and, as examples, there may be mentioned:
2-chloro-5-chloromethylpyridine,
2-chloro-5-chloromethylthiazole,
5-chloromethyl-2-trifluoromethylpyridine, and the like.

In the process e), the compounds of the formula (Id) are a part of the compounds of the formula (I) which can be prepared by the above process d).

In the process f), the compounds of the formula (VIII) as a starting material mean ones based on the aforementioned definitions of R[1], R[2], R[4], Z and M.

In the formula (VIII), R[1], R[2], R[4], Z and M preferably have the meanings already given above.

The compounds of the formula (VIII) are novel and, in general, can be obtained when compounds of the formula (XV)

$$\begin{array}{c} R^1 \quad R^2 \quad O \\ | \quad\quad | \quad\quad \| \\ Z-CH-N-C-NH_2 \end{array} \quad \text{(XV)}$$

wherein R[1], R[2] and Z have the same meanings as mentioned above,
are reacted with compounds of the formula (XIV)

$$R^4-M \quad \text{(XIV)}$$

wherein R[4] and M have the same meanings as mentioned above.

The above compounds of the formula (XV) in general can be obtained when the aforementioned compounds of the formula (III) are reacted with urea.

The above compounds of the formula (XVI) are well-known in the field of organic chemistry, and as examples there may be mentioned: methyl, ethyl, n-propyl, iso-propyl and 3-pyridylmethyl esters of p-toluenesulfonic acid, and monochlorides of methane, ethane and propane, etc.

As examples of the compounds of the formula (XV), there may be mentioned:
1-(2-chloro-5-pyridylmethyl)urea, 1-(2-chloro-5-thiazolyl)urea, 1-(2-chloro-5-pyridyl)-1-methylurea, 1-[1-(2-chloro-5-pyridyl)ethyl]urea, and the like.

As examples of the compounds of the formula (VIII), there may be mentioned:
hydrochloride or p-toluenesulfonate of 1-(2-chloro-5-pyridylmethyl)-2-methylisourea,
hydrochloride of 1-(2-chloro-5-pyridylmethyl)-2-methylisourea, or p-toluenesulfonate thereof,
hydrochloride of 1-(2-chloro-5-thiazolylmethyl)-2-methylisourea, or p-toluenesulfonate, and the like.

In the process g), the compounds of the formula (IX) as a starting material mean ones based on the aforementioned definitions of R[7], R[2] and Z.

The compounds of the formula (IX) are a part of the compounds of the formula (I) which can be prepared by the above process b) or c), and as examples there may be mentioned:
1-[1-(2-chloro-5-pyridyl)ethylamino]-1-dimethylamino-2-nitroethylene and
1-[1-(2-chloro-5-thiazolyl)ethylamino]-1-dimethylamino-2-nitroethylene.

The compounds of the formula (X) mean ones based on the aforementioned definition of R[4].

In the formula (x), R[4] has the meaning already given above.

The compounds of the formula (X) are well-known in the field of organic chemistry, and as examples there may be mentioned: methanol, ethanol, propanol, phenol, and the like.

Suitable diluents in the process a) are all inert solvents.

These preferentially include water; aliphatic-, cycloaliphatic- and aromatic- hydrocarbons optionally chlorinated such as hexane, cyclohexane, petroleum ether, ligroin, benzene, toluene, xylene, methylene chloride, chloroform, carbon tetrachloride, ethylene chloride, trichloroethylene, chlorobenzene and the like; ethers such as diethyl ether, methyl ethyl ether, di-isopropyl ether, dibutyl ether, propylene oxide, dioxane, tetrahydrofuran and the like; ketones such as acetone, methylethyl ketone, methyl-iso-propyl ketone, methyl-iso-butyl ketone; nitriles such as acetonitrile, propionitrile, acrylonitrile and the like; alcohols such as methanol, ethanol, iso-propanol, butanol, ethylene glycol and the like; esters such as ethyl acetate, amyl acetate; acid amides such as dimethyl formamide, dimethyl acetamide and the like; and sulfones and sulfoxides such as dimethyl sulfoxide, sulfolane and the like; and bases, for example, such as pyridine.

In the process a), the reaction temperature can be varied within a wide range. In general, the reaction is carried out at a temperature of from about 0° C. to 150° C., preferably from about 20° C. to about 90° C.

In general, the reaction is preferably carried out under normal pressure, or also elevated or reduced pressure.

In carrying out the process a), for instance, about 0.9 to slightly more than one mole of the compounds of the formula (III) may be employed per mole of the compounds of the formula (II), and the mixture is reacted in the presence of inert solvents under heat-reflux until the generation of mercaptan ceases, so that the desired compounds of the formula (I) can be obtained.

In carrying out the process b), suitable diluents include the same solvents as exemplified for the process a).

In the process b), the reaction temperature can be varied within a wide range. For example, the reaction is carried out at a temperature in the range of from about 0° C. to about 150° C., preferably from about 20° C. to about 90° C.

In general, the reaction is preferably carried out under normal pressure, or also elevated or reduced pressure.

In carrying out process b), for instance, equi-molar to slightly more than one mole of the compounds of the formula (IV) may be employed per mole of the compounds of the formula (Ia), and the mixture is reacted in the presence of inert solvents, so that the desired compounds of the formula (I) can be obtained.

In carrying out the process c), suitable diluents include the same solvents as exemplified for the process a).

In the process c), the reaction temperature can be varied within a wide range. For example, the reaction is carried out a temperature in the range of from about 0° C. to about 150° C., preferably from about 20° C. to about 90° C.

In general, the reaction is preferably carried out under normal pressure, or also elevated or reduced pressure.

In carrying out process c), for instance, about 0.9 to slightly more than one mole of the compounds of the formula (III) may be employed per mole of the compounds of the formula (V), and the mixture is reacted in the presence of inert solvents under heat-reflux so that the desired compounds of the formula (I) can be obtained.

In carrying out the process d), suitable diluents include the same solvents as exemplified for the process a).

The process d) may be carried out in the presence of acid binders, such as hydroxide, hydride, carbonate, bicarbonate and alcoholate alkali metal, and tertiary amines, for examples, triethylamine and diethylaniline, and pyridine.

In the process d), the reaction temperature can be varied within a wide range. For example, the reaction is carried out at a temperature in the range of from about 0° C. to boiling point of the reaction mixture, preferably from about 0° C. to about 80° C.

In general, the reaction is preferably carried out under normal pressure, or also elevated or reduced pressure.

In carrying out the process d), for instance, equi-molar to about 1.2 mole, preferably equi-molar to about 1.1 mole of the compounds of the formula (VII) may be employed per mole of the compounds of the formula (VI), and the mixture is reacted in the presence of inert solvents, for example dimethylsulfoxide, and in the presence of a base, sodium hydride, so that the desired compounds of the formula (I) can be obtained.

In carrying out the process e), suitable diluents include the same solvents as exemplified for the process a).

In the process e), the reaction temperature can be varied within a wide range. For example, the reaction is carried out at a temperature in the range of from about 0° C. to about 150° C., preferably from about 20° C. to about 90° C.

In general, the reaction is preferably carried out under normal pressure, or also elevated or reduced pressure.

In carrying out the process e), for instance, equi-molar to slightly more than one more of the compounds of the formula (IV) may be employed per mole of the compounds of the formula (Id), and the mixture is reacted in the presence of inert solvents, so that the desired compounds of the formula (I) can be obtained.

In carrying out the process f), for instance, the compounds of the formula (VIII) dissolved in concentration sulfuric acid are reacted with fuming nitric acid having a purity of higher than 98% at a low temperature, preferably at 0° C. or less than 0° C., so that the desired compounds of the formula (I) can be obtained.

In carrying out the process g), suitable diluents include the solvents as exemplified for the process a), excluding alcohols.

In the process g), the reaction temperature can be varied within a wide range. For example, the reaction is carried out at a temperature in the range of from about 0° C. to about 120° C., preferably from about 50° C. to about 90° C.

In general, the reaction is preferably carried out under normal pressure, or also elevated or reduced pressure.

In carrying out process g), for instance, an excess molar amount of the compounds of the formula (X) may be employed per mole of the compounds of the formula (IX), and the mixture is reacted under heat-reflux, so that the desired compounds of the formula (I) can be obtained.

The active compounds are well tolerated by plants, have a favorable level of toxicity to warm-blooded animals, and can be used for combating arthropod pests, especially insects which are encountered in agriculture, in forestry, in the protection of stored products and of materials, and in the hygiene field. They are active against normally sensitive and resistant species and against all or some stages of development. The above-mentioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and *Scutigera* spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera; for example *Blatta orientalis, Periplaneta americana, Leucophaea maderae, Blattella germanica, Acheta domesticus,* Gryllotalpa spp., *Locusta migrato ria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci,* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., Spodoptera exigua, Mamestra brassicae, Panolis flammea, Prodenia litura, Spodoptera spp., Trichoplusia ni, Carpocapsa pomonella, Pieris spp., Chilo spp., Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Acanthoscelides obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera for example Diprion spp., Hoplocampa spp., Lasius spp., *Monomorium pharaonis* and Vespa spp.;

from the order of the Diptera, for example Aedes spp., Anopheles spp., Culux spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bilio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Aranina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The plant-parasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp., and Trichodorus spp.

Furthermore, in the field of veterinary medicine, the novel compound of the present invention can effectively be employed for combating a variety of noxious animal-parasitic pests (internal- and external-parasitic pests), e.g., parasitic insects and nematodes. Such animal-parasitic pests may be exemplified as follows:

From the class of insects, e.g., Gastrophilus spp., Stomoxys spp., Tricodectes spp., Rhodius spp., *Ctenocephalides canis* and the like.

The active compounds can be converted into the customary formulations, such as solutions, emulsions, wet-table powders, suspensions, powders, foams, pastes, granules, aerosols, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations can be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethyl-sulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or lactices, such as gum arabic, polyvinyl alcohol and polyvinyl acetate, can be used in the formulation.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese boron, copper, cobalt, molybdenum and zinc.

The formulations in general contain from 0.1 to 95 percent by weight of active compound, preferably from 0.5 to 90 per cent by weight.

The active compounds according to the invention can be present in their commercially available formulations and in the use forms, prepared from these formulations, as a mixture with other active compounds, such as insecticides, baits, sterilising agents, acaricides, nematicides, fungicides, growth-regulating substances or herbicides. The insecticides include, for example, phosphates, carbamates, carboxylates, chlorinated hydrocarbons, phenylureas, substances produced by microorganisms.

The active compounds according to the invention can furthermore be present in their commercially available formulations and in the use forms, prepared from these formulations, as a mixture with synergistic agents. Synergistic agent are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 100% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substances.

The preparation and use of the active compounds according to the invention can be seen from the following examples.

PREPARATIVE EXAMPLE

EXAMPLE 1

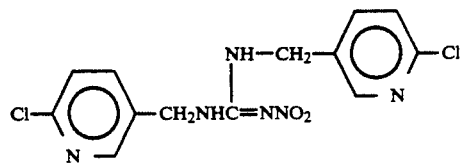

1-2-(chloro-5-pyridylmethyl)-2-methyl-3-nitroisothiourea (1.0 g) was dissolved in ethanol (20 ml) and to the solution was added 2-chloro-5-aminomethylpyridine (0.55 g) at room temperature, followed by one day stirring at 30° C. The ethanol in the solution was distilled off under reduced pressure and it was purified on a chromatographic column (the eluent was a mixture of methanol and chloroform) so as to obtain the desired 1,3-bis-(2-chloro-5-pyridylmethyl)-2-nitroguanidine (1.0 g) having a melting point in the range of from 179° to 182° C.

REFERENTIAL EXAMPLE 1

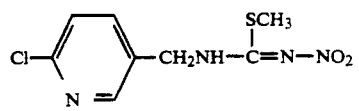

To a solution of 2-methyl-3-nitroisothiourea (15.0 g) in dimethylsulfoxide (100 ml) was gradually added sodium hydride (oil free 2.9 g) at 5° C., while being stirred for one hour. Thereafter, 2-chloro-5-chloromethyl pyridine (18.0 g) was added to the solution at a temperature in the range of from 5° to 10° C., followed by overnight stirring thereof at room temperature. After the dimethylsulfoxide in the solution was distilled off under reduced pressure, the resulting residue was purified on a chromatographic column (the eluent was a mixture of ethanol and chloroform), so as to obtain the desired 1-(2-chloro-5-pyridylmethyl)-2-methyl-3-nitroisothiourea (2.0 g) having a melting point in the range of from 141° to 143° C.

REFERENTIAL EXAMPLE 2

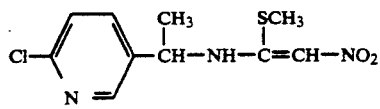

A mixture of 1-(2-chloro-5-pyridyl)ethylamine (4.7 g), 1,1-bis-methylthio-2-nitroethylene (5.0 g) and ethanol (50 ml) was refluxed under heating until the generation of mercaptan ceased. Then, the ethanol was distilled off from the mixture under reduced pressure and the resulting residue was purified on a chromatographic column (the eluent mixture=ethanol+chloroform) to obtain the desired 1-{1-(2-chloro-5-pyridyl)e- thylamino}-1-methylthio-2-nitroethylene (3.3 g) having a melting point in the range of from 136° to 140° C.

REFERENTIAL EXAMPLE 3

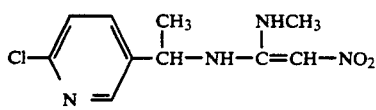

To a solution comprising 1-{1-(2-chloro-5-pyridyl)ethylamino}-1-methylthio-2-nitroethylene (2.7 g) in ethanol (50 ml) was added dropwise an aqueous solution of methylamine (40%, 3 g) at 50° C., followed by two hours stirring at the same temperature.

Upon cooling the solution to room temperature, the desired product was separated in the form of crystals, which were filtered and washed with ethanol to obtain the desired 1-{1-(2-chloro-5-pyridyl)ethylamino}-1-methylamino-2-nitroethylene (1.5 g) having a melting point in the range of from 183° to 186° C.

The compounds of the following formula (I),

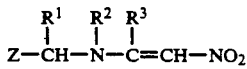

which can be prepared in the same way as in the above Referential Examples 2 and 3 are shown in Table 1.

The compounds of the following formula (I),

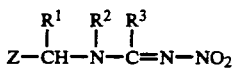

which can be prepared in the same way as in the above Example 1 and Referential Example 1 are shown in Table 2.

TABLE 1

$$Z-\overset{R^1}{\underset{|}{C}H}-\overset{R^2}{\underset{|}{N}}-\overset{R^3}{\underset{|}{C}}=CH-NO_2$$

| Comp. No. | Z | $R^1$ | $R^2$ | $R^3$ |
|---|---|---|---|---|
| 1 | 2-trifluoromethyl-5-thiazolyl | $C_3H_7$-n | H | $SC_2H_5$ |
| 2 | 2-trifluoromethyl-5-thiazolyl | $CH_3$ | H | $SCH_3$ |
| 3 | 2-chloro-5-pyridyl | $C_4H_9$-n | H | $NHCH_2CH=CH_2$ |
| 4 | 2-chloro-5-pyridyl | $CH_3$ | H | $NHCH_2CH=CH_2$ |
| 5 | 2-chloro-5-pyridyl | $CH_3$ | $CH_3$ | −NH−CH$_2$−(2-chloro-5-pyridyl) |
| 6 | 2-chloro-5-oxazolyl | $CH_3$ | H | −N($C_2H_5$)−(2-chloro-5-pyridyl) |
| 7 | 2-chloro-5-pyridyl | CN | H | $SCH_3$ |
| 8 | 2-chloro-5-pyridyl | CN | $CH_3$ | $SCH_3$ |
| 9 | 2-chloro-5-pyridyl | CN | H | $NH_2$ |
| 10 | 2-chloro-5-pyridyl | CN | $CH_3$ | $NH_2$ |
| 11 | 2-chloro-5-pyridyl | CN | H | $NHCH_3$ |
| 12 | 2-chloro-5-pyridyl | CN | $CH_3$ | $NHCH_3$ |
| 13 | 2-chloro-5-pyridyl | CN | $CH_3$ | $N(CH_3)_2$ |
| 14 | 2-chloro-5-pyridyl | $CH_3$ | H | $OC_2H_5$ |

TABLE 2

$$Z-\overset{R^1}{\underset{|}{C}H}-\overset{R^2}{\underset{|}{N}}-\overset{R^3}{\underset{|}{C}}=N-NO_2$$

| Comp. No. | Z | $R^1$ | $R^2$ | $R^3$ |
|---|---|---|---|---|
| 15 | 2-trifluoromethyl-5-pyridyl | $C_2H_5$ | H | $SCH_3$ |
| 16 | 2-trifluoromethyl-5-pyridyl | $C_3H_7$-n | H | $SCH_2C\equiv CH$ |
| 17 | 2,3-dichloro-5-pyridyl | H | H | S−(cyclohexyl) |
| 18 | 3-methyl-5-isoxazolyl | H | H | S−(4-chlorophenyl) |

TABLE 2-continued $$Z-CH(R^1)-N(R^2)-C(R^3)=N-NO_2$$

| Comp. No. | Z | R¹ | R² | R³ | |
|---|---|---|---|---|---|
| 19 | 2-chloro-5-thiazolyl | H | $C_2H_5$ | $-SCH_2-C_6H_4-Cl$ (p) | |
| 20 | 2-chloro-5-thiazolyl | H | H | $OCH_3$ | |
| 21 | 2-chloro-5-pyridyl | H | H | $OCH_3$ | |
| 22 | 2-chloro-5-pyridyl | H | $CH_3$ | $OCH_3$ | |
| 23 | 2-methyl-1,3,4-oxadiazol-5-yl | H | H | $OCH_3$ | |
| 24 | 1,2,5-thiadiazol-3-yl | H | H | $OCH_3$ | |
| 25 | 3-methyl-5-isoxazolyl | $CH_3$ | H | $OC_2H_5$ | |
| 26 | 2-chloro-5-thiazolyl | H | H | $OC_3H_{7\text{-}n}$ | |
| 27 | 1,2,5-thiadiazol-3-yl | H | H | $OC_3H_{7\text{-}iso}$ | |
| 28 | 2-pyrazinyl | $C_3H_{7\text{-}n}$ | H | $-OCH_2-(3\text{-pyridyl})$ | |
| 29 | 2-chloro-5-pyridyl | H | $CH_2C\equiv CH$ | $-NHCH_3$ | |
| 30 | 2-cyano-5-pyridyl | H | $CH_3$ | $-NHC_2H_5$ | |
| 31 | 2-chloro-5-thiazolyl | H | H | $-NHCH_2CCl=CH_2$ | |
| 32 | 2-methyl-5-pyridyl | H | $CH_3$ | $-NHCH_2CCl=CH_2$ | |
| 33 | 2-chloro-5-pyridyl | H | H | $-NHCH_2CH=CH_2$ | |
| 34 | 2-chloro-5-pyridyl | H | $CH_3$ | $-NHCH_2CH=CH_2$ | |
| 35 | 2-methyl-5-pyrazinyl | H | $CH_3$ | $-NHCH_2CH=CH_2$ | |
| 36 | 2-chloro-5-pyridyl | H | H | $-NHCH_2C\equiv CH$ | $n_D^{50}$ 1.15955 |
| 37 | 2-chloro-5-pyridyl | H | $CH_3$ | $-NHCH_2C\equiv CH$ | |
| 38 | 2-chloro-5-pyridyl | H | H | $-NH-C_6H_5$ | |
| 39 | 2-chloro-5-pyridyl | H | $CH_3$ | $-NH-C_6H_5$ | |
| 40 | 2-chloro-5-thiazolyl | H | $CH_3$ | $-NH-C_6H_4-Cl$ (p) | |
| 41 | 2-methyl-5-pyrazinyl | H | $CH_3$ | $-NHCH_2-C_6H_5$ | |

TABLE 2-continued $$\begin{array}{c} R^1 \quad R^2 \quad R^3 \\ | \quad | \quad | \\ Z-CH-N-C=N-NO_2 \end{array}$$

| Comp. No. | Z | $R^1$ | $R^2$ | $R^3$ | |
|---|---|---|---|---|---|
| 42 | 2-chloro-5-pyridyl | H | H | —NHCH$_2$—C$_6$H$_5$ | |
| 43 | 2-chloro-5-pyridyl | H | CH$_3$ | —NHCH$_2$—C$_6$H$_5$ | |
| 44 | 2-chloro-5-pyridyl | H | H | —NHCH$_2$—C$_6$H$_4$—Cl (4-Cl) | |
| 45 | 2-chloro-5-pyridyl | H | CH$_3$ | —NHCH$_2$—C$_6$H$_4$—Cl (4-Cl) | |
| 46 | 2-chloro-5-pyridyl | H | CH$_3$ | —NHCH$_2$—C$_6$H$_4$—Cl (3-Cl) | |
| 47 | 1,2,5-thiadiazol-3-yl | H | H | —NH—C$_6$H$_4$—Cl (4-Cl) | |
| 48 | 2-chloro-5-pyridyl | H | H | —NH—(6-chloro-pyridin-3-yl) | |
| 49 | 2-chloro-5-pyridyl | H | CH$_3$ | —NH—(6-chloro-pyridin-3-yl) | |
| 50 | 2-chloro-5-pyridyl | H | H | —NH—CH$_2$—(6-chloro-pyridin-3-yl) | mp. 179~182° C. |
| 51 | 2-chloro-5-pyridyl | H | CH$_3$ | —NH—CH$_2$—(6-chloro-pyridin-3-yl) | |
| 52 | 2,3-dichloro-5-pyridyl | H | cyclopentyl(H)(CH$_3$) | —N(CH$_3$)$_2$ | |
| 53 | 2-chloro-5-pyridyl | H | CH$_2$C≡CH | —N(CH$_3$)$_2$ | |

TABLE 2-continued $$Z-\overset{R^1}{\underset{}{C}}H-\overset{R^2}{\underset{}{N}}-\overset{R^3}{\underset{}{C}}=N-NO_2$$

| Comp. No. | Z | R¹ | R² | R³ | |
|---|---|---|---|---|---|
| 54 | 2,3-dimethyl-5-pyridyl | H | 4-chlorophenyl | $-\underset{CH_3}{N}-C_2H_5$ | |
| 55 | 2-chloro-5-pyridyl | H | H | $-\underset{CH_3}{N}-CH_2CH=CH_2$ | |
| 56 | 2-chloro-5-pyridyl | H | H | $-\underset{CH_3}{N}-CH_2CH=CH_2$ | |
| 57 | 2-chloro-5-pyridyl | H | 3-bromobenzyl (CH₂-C₆H₄-Br) | $-\underset{CH_3}{N}-CH_2CH=CHCl$ | |
| 58 | 2-methyl-5-pyrazinyl | H | H | $-\underset{CH_3}{N}-(4\text{-}Cl\text{-}C_6H_4)$ | |
| 59 | 2-methyl-5-pyridyl | H | H | $-\underset{CH}{N}-CH_2-(6\text{-chloropyridin-3-yl})$ | |
| 60 | 2-bromo-5-pyridyl | H | H | $-\underset{C_2H_5}{N}-CH_2-(6\text{-chloropyridin-3-yl})$ | |
| 61 | 2-chloro-5-pyrimidinyl | H | H | $-\underset{C_2H_5}{N}-CH_2-\text{cyclohexyl}$ | |
| 62 | 2-fluoro-5-thiazolyl | H | CH₂-(6-chloropyridin-3-yl) | $-\underset{C_3H_{7\text{-}iso}}{N}-CH_2C\equiv CH$ | |
| 63 | 1,2,5-oxadiazol-3-yl | H | H | $-N[CH_2-(6\text{-chloropyridin-3-yl})]_2$ | |
| 64 | 2-chloro-5-pyridyl | H | H | pyrrolidin-1-yl | mp. 169~172° C. |
| 65 | 2-chloro-5-pyridyl | CH₃ | CH₂-(6-chloropyridin-3-yl) | piperidin-1-yl | |

TABLE 2-continued $$Z-\overset{R^1}{\underset{|}{C}}H-\overset{R^2}{\underset{|}{N}}-\overset{R^3}{\underset{|}{C}}=N-NO_2$$

| Comp. No. | Z | R¹ | R² | R³ |
|---|---|---|---|---|
| 66 | 2-chloro-5-pyridyl | H | H | 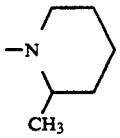 |
| 67 | 2-chloro-5-pyridyl | H | H |  |
| 68 | 2-chloro-5-pyridyl | H | H | 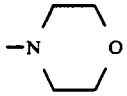 |
| 69 | 2-chloro-5-pyridyl | H | H | 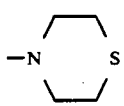 |
| 70 | 2-chloro-5-pyridyl | H | H | 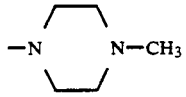 |
| 71 | 2-chloro-5-pyridyl | H | CH₃ | 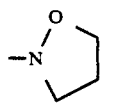 |
| 72 | 2-chloro-5-pyridyl | H | H | NHOCH₃ |
| 73 | 2-chloro-5-pyridyl | H | CH₃ | NHOCH₃ |
| 74 | 2-chloro-5-pyridyl | H | H | N(CH₃)OCH₃ |
| 75 | 2-chloro-5-pyridyl | H | CH₃ | N(CH₃)OCH₃ |
| 76 | 2-chloro-5-pyridyl | H | OCH₃ | NH₂ |
| 77 | 2-chloro-5-pyridyl | H | OCH₃ | NHCH₃ |
| 78 | 2-chloro-5-pyridyl | H | OCH₃ | N(CH₃)₂ |
| 79 | 2-chloro-5-pyridyl | H | H | NHNH₂ |
| 80 | 2-chloro-5-pyridyl | H | H | NHNHCH₃ |
| 81 | 2-chloro-5-thiazolyl | H | H | NHNHCH₃ |
| 82 | 2-chloro-5-thiazolyl | H | CH₃ | NHN(CH₃)₂ |
| 83 | 2-chloro-5-pyridyl | H | H | NHOH |
| 84 | 2-chloro-5-pyridyl | H | CH₃ | NHOH |
| 85 | 2-chloro-5-pyridyl | CN | H | SCH₃ |
| 86 | 2-methyl-5-pyrazinyl | CN | CH₃ | OC₂H₅ |
| 87 | 2-chloro-5-pyridyl | CN | H | NHCH₃ |
| 88 | 2-chloro-5-pyridyl | CN | H | N(CH₃)₂ |
| 89 | 2-chloro-5-pyridyl | H | H | NHCH₂CH₂OC₂H₅ |
| 90 | 2-chloro-5-thiazolyl | H | H | NHCH₂CH₂SH |
| 91 | 2-chloro-5-pyridyl | H | H | NHCH₂CH₂NH₂ |
| 92 | 2-chloro-5- | H | H | NHCH₂COOC₂H₅ |

TABLE 2-continued $$Z-\overset{R^1}{\underset{|}{C}H}-\overset{R^2}{\underset{|}{N}}-\overset{R^3}{\underset{|}{C}}=N-NO_2$$

| Comp. No. | Z | $R^1$ | $R^2$ | $R^3$ | |
|---|---|---|---|---|---|
| 93 | 2-bromo-5-pyridyl thienyl | H | $CH_3$ | $NH_2$ | mp. 159~161° C. |
| 94 | 2-bromo-5-thienyl | H | $CH_3$ | $NHCH_3$ | |
| 95 | 2-bromo-5-thienyl | H | $CH_3$ | $N(CH_3)_2$ | |
| 96 | 2-bromo-5-thienyl | H | H | $NHCH_3$ | |
| 97 | 2-chloro-5-pyridyl | H | $CH_3$ | N—CHO<br>\|<br>$CH_3$ | mp. 99~101° C. |
| 98 | 2-chloro-5-pyridyl | H | H | $NHCOCH_3$ | |
| 99 | 2-chloro-5-pyridyl | H | $CH_3$ | $NHCOCH_3$ | |
| 100 | 2-chloro-5-pyridyl | H | H | 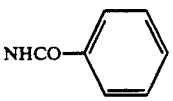 | |
| 101 | 2-chloro-5-pyridyl | H | $CH_3$ | 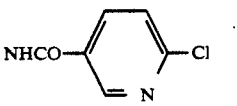 | |

BIOLOGICAL TESTS

Comparative compound E-1

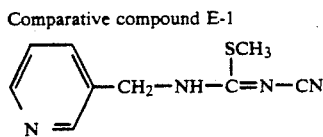

[disclosed in Japanese Patent Laid-open No. 233903/1988]

EXAMPLE 5

Biological test

Test on *Mephotettix cincticeps* having resistance to organophosphorus agents:

Preparation of a test chemical

Solvent: 3 parts by weight of xylene
Emulsifier: 1 part by weight of polyoxyethylene alkyl phenyl ether.

To form a suitable preparation, 1 part by weight of the active compound was mixed with the aforesaid amount of the solvent containing the aforesaid amount of the emulsifier. The mixture was diluted with water to a predetermined concentration.

Testing method

Onto rice plants, about 10 cm tall, planted in pots each having a diameter of 12 cm was sprayed 10 ml per pot of the water-dilution of each active compound in a predetermined concentration prepared as above. The sprayed chemical was dried, and a wire net having a diameter of 7 cm and a height of 14 cm was put over each pot, and 30 female imagoes of *Nephotettix cincticeps* showing resistance to organophosphorus agents were released into the net. The pots were each placed in a constant temperature chamber and the number of dead insects was examined 2 days later, and the Insect mortality was calculated.

As a result, for instance, compound Nos. 36 and 50 showed 100% kill at 50 ppm active ingredient.

On the other hand, as comparison, E-1 showed no killing effect at 50 ppm a.i.

EXAMPLE 6

Biological test

Test on planthoppers

Testing method

A water dilution in a predetermined concentration of the active compound prepared as in Example 5 was sprayed onto rice plants, about 10 cm tall, grown in pots with a diameter of 12 cm in an amount of 10 ml per pot. The sprayed chemical was dried, and a wire net, 7 cm in diameter and 14 cm tall, was put over each of the pots. Thirty female imagoes of *Nilaparvata lugens* Stal of a strain which showed resistance to organophosphorus chemicals were released into the net. The pots were left to stand in a constant temperature chamber and the number of dead insects was examined two days later. The kill ratio was then calculated.

In the same way as above, the insect mortality was calculated on *Sogatella furcifera* Horvath and organophosphorus-resistant *Laodelphax striatellus* Fallen.

As a result, for instance, compound Nos. 36 and 50 showed 100% kill at 50 ppm active ingredient.

On the other hand, as comparison, E-1 showed no killing effect at 50 ppm a.i.

We claim:
1. A nitro compound of the formula

$$Z-\underset{\underset{H}{|}}{C}H-\underset{\underset{H}{|}}{N}-\underset{\underset{H}{|}}{C}=\underset{\underset{H}{|}}{C}-NO_2 \quad (I)$$

wherein
$R^1$ is cyano or $C_{1-4}$ alkyl,
$R^2$ is hydrogen, $C_{1-6}$ alkyl, $C_{3-4}$ alkenyl, $C_{3-4}$ alkynyl, $C_{3-8}$ cycloalkyl optionally substituted by $C_{1-2}$ alkyl, phenyl optionally substituted by halogen, benzyl optionally substituted by halogen, $C_{1-4}$ alkoxy or —$(CH_2)_n$—Z, in which n is 1 or 2,
$R^3$ is $$-O-R^4, -S-R^4 \text{ or } -\underset{\underset{R^6}{|}}{N}-R^{5},$$

in which
$R^4$ is $C_{1-6}$ alkyl, $C_{3-4}$ alkenyl, $C_{3-4}$ alkynyl, $C_{3-8}$ cycloalkyl, phenyl optionally substituted by halogen, benzyl optionally substituted by halogen, or —$(CH_2)_n$—Z,
$R^5$ and $R^6$ are the same or different and stand for hydrogen, $C_{1-9}$ alkyl optionally substituted by at least one substituent selected from the group consisting of mercapto, $C_{1-2}$ alkoxy, $C_{3-6}$ cycloalkyl, amino, $C_{1-2}$ mono-alkylamino, $C_{2-4}$ (in total) dialkylamino, $C_{1-2}$ alkoxy-carbonyl and cyano; or
$R^5$ and $R^6$ are the same or different and stand for $C_{3-4}$ alkenyl optionally substituted by halogen, $C_{3-4}$ alkynyl, phenyl, benzyl, $C_{1-4}$ alkoxy, hydroxy, formyl, $C_{1-4}$ alkylamino, $C_{2-4}$ (in total) dialkylamino, amino, acetyl, benzoyl, 6-chloronicotinoyl, pyridyl optionally substituted by chlorine or methyl, or —$CH_2$—Z, or
$R^5$ and $R^6$ may form, together with the adjacent nitrogen atom, a pyrrolidino, piperidino, 2-methylpiperidino, morpholino, piperazino or 1-isoxazolyl group, each optionally substituted by $C_{1-2}$ alkyl, and
Z is a pyridyl, thiazolyl, isoxazolyl, thiadiazolyl, pyrazolyl, oxazolyl, pyrimidinyl or pyrazinyl group, each optionally substituted by halogen or $C_{1-4}$-alkyl,
with the exception of the case were $R^1$ is $C_{1-4}$ alkyl, $R^2$ is hydrogen or $C_{1-4}$-alkyl, $R^3$ is —S—$R^4$ or $$-\underset{\underset{R^6}{|}}{N}-R^{5}$$

in which $R^4$ is $C_{1-4}$ alkyl, $R^5$ and $R^6$ are hydrogen or $C_{1-4}$ alkyl, and Z is a 5- or 6-membered heterocyclic group having at least one nitrogen atom which may be substituted by halogen or $C_{1-4}$ alkyl.

2. A compound according to claim 1, wherein
$R^1$ is methyl, ethyl or n-propyl,
$R^2$ is hydrogen, $C_{1-4}$ alkyl, allyl, propargyl, $C_{5-6}$ cycloalkyl optionally substituted by methyl, phenyl optionally substituted by halogen, benzyl optionally substituted by halogen, $C_{1-3}$ alkoxy or —$CH_2$—$Z^1$ in which
$Z^1$ is pyridyl optionally substituted by halogen,
$R^3$ is $$-O-R^4, -S-R^4 \text{ or } -\underset{\underset{R^6}{|}}{N}-R^{5}$$

in which
$R^4$ is $C_{1-4}$ alkyl, allyl, $C_{3-6}$ cycloalkyl, phenyl optionally substituted by halogen, benzyl optionally substituted by halogen or —$CH_2$—$Z^1$, and
$R^5$ and $R^6$ are hydrogen, $C_{1-6}$ alkyl optionally substituted by at least one substituent selected from the group consisting of mercapto, methoxy, cyclohexyl, amino, methylamino, dimethylamino, methoxycarbonyl and cyano, allyl optionally substituted by chlorine, propargyl, phenyl optionally substituted by chlorine, benzyl optionally substituted by chlorine, $C_{1-3}$ alkoxy, hydroxy, formyl, $C_{1-3}$ alkylamino, dimethylamino, amino, acetyl, benzoyl, 6-chloronicotinoyl, pyridyl optionally substituted by chlorine or methyl, or —$CH_2$—$Z^2$ in which $Z^2$ represents pyridyl optionally substituted by halogen, or 5-thiazolyl optionally substituted by chlorine, or in addition $R^5$ and $R^6$ may form, together with the adjacent nitrogen atom, a pyrrolidino, piperidino, 2-methylpiperidino, morpholino, piperazino or 1-isoxazolyl group which may be substituted by methyl.

3. A compound according to claim 1, wherein
$R^1$ is methyl or ethyl,
$R^2$ is hydrogen, methyl, ethyl, n-propyl, allyl, propargyl, cyclohexyl, phenyl optionally substituted by chlorine, benzyl optionally substituted by chlorine, $C_{1-2}$ alkoxy or 2-chloro-5-pyridylmethyl, and
$R^3$ is $$-\underset{\underset{R^6}{|}}{N}-R^{5}$$

in which $R^5$ and $R^6$ are hydrogen, $C_{1-4}$ alkyl optionally substituted by at least one substituent selected from the group consisting of mercapto, methoxy, cyclohexyl, amino, methylamino, dimethylamino, methoxycarbonyl and cyano, allyl optionally substituted by chlorine, benzyl optionally substituted by chlorine, $C_{1-2}$ alkoxy, hydroxy, formyl, $C_{1-2}$ alkylamino, dimethylamino, amino, acetyl of benzoyl, 6-chloronicotinoyl, 2-chloro-5-pyridyl, 2-chloro-5-pyridylmethyl or 2-chloro-5-thiazolylmethyl, or in addition $R^5$ and $R^6$ may represent, together with the adjacent nitrogen atom, pyrrolidino, piperidino, 2-methylpiperidino, morpholino, piperazino or 1-isoxazolyl.

4. A compound according to claim 1, wherein
$R^1$ is methyl or ethyl,
$R^2$ is hydrogen, methyl, ethyl, n-propyl, allyl, propargyl, cyclohexyl, phenyl optionally substituted by chlorine, benzyl optionally substituted by chlorine, $C_{1-2}$ alkoxy or 2-chloro-5-pyridylmethyl, and
$R^3$ is

in which $R^5$ and $R^6$ are hydrogen, $C_{1-4}$ alkyl optionally substituted by at least one substituent selected from the group consisting of mercapto, methoxy, cyclohexyl, amino, methylamino, dimethylamino, methoxycarbonyl and cyano, allyl optionally substituted by chlorine, benzyl optionally substituted by chlorine, $C_{1-2}$ alkoxy, hydroxy, formyl, $C_{1-2}$ alkylamino, dimethylamino, amino, acetyl, benzoyl, 6-chloronicotinoyl, 2-chloro-5-pyridyl, 2-chloro-5-pyridylmethyl or 2-chloro-5-thiazolylmethyl, or in addition $R^5$ and $R^6$ may represent, together with the adjacent nitrogen atom, pyrrolidino, piperidino, 2-methylpiperidino, morpholino, piperazino or 1-isoxazolyl.

5. A compound according to claim 1, wherein
$R^1$ is methyl
$R^2$ is hydrogen, methyl, ethyl, allyl, propargyl, methoxy or 2-chloro-5-pyridylmethyl,
$R^3$ is

in which $R^5$ and $R^6$ are hydrogen, $C_{1-2}$ alkyl optionally substituted by at least one substituent selected from the group consisting of mercapto, methoxy, cyclohexyl, amino, methylamino, dimethylamino, methoxycarbonyl and cyano, allyl, 2-chloroallyl, benzyl, 3- or 4-chlorobenzyl, methoxy, hydroxy, formyl, methyamino, dimethylamino, amino, acetyl, benzoyl, 6-chloronicotinoyl, 2-chloro-5-pyridyl or 2-chloro-5-pyridylmethyl,
Z is 2-chloro-5-pyridyl.

6. A compound according to claim 1, wherein such compound is 1-{N-[1-(2-chloro-5-pyridyl)ethyl]-N-methylamino}-1-(2-chloro-5-pyridylmethyl)amino-2-nitroethylene of the formula

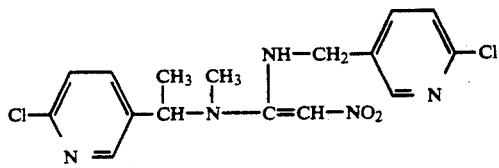

7. An insecticidal composition comprising an insecticidally effective amount of a compound according to claim 1 and a diluent.

8. A method of combating insects which comprises applying to such insects or to an insect habitat an insecticidally effective amount of a compound according to claim 1.

9. The method according to claim 8, wherein such compound is 1-{N-[1-(2-chloro-5-pyridyl)ethyl]-N-methylamino}-1-(2-chloro-5-pyridylmethyl)amino-2-nitroethylene.

* * * * *